United States Patent [19]

McKnight

[11] 4,112,735
[45] Sep. 12, 1978

[54] DETECTION OF BUBBLES IN A LIQUID

[75] Inventor: James Alan McKnight, Altrincham, England

[73] Assignee: United Kingdom Atomic Energy Authority, England

[21] Appl. No.: 829,134

[22] Filed: Aug. 30, 1977

[30] Foreign Application Priority Data

Sep. 13, 1976 [GB] United Kingdom ............... 37927/76

[51] Int. Cl.² .......................................... G01N 29/02
[52] U.S. Cl. ..................................... 73/19; 73/432 PS
[58] Field of Search ................... 73/19, 61 R, 432 PS, 73/194 A

[56] References Cited

U.S. PATENT DOCUMENTS

| 3,208,286 | 9/1965 | Richard | 73/432 PS |
| 3,741,014 | 6/1973 | Tamura | 73/194 A |
| 3,802,271 | 4/1974 | Bertelson | 73/61 R |
| 3,940,731 | 2/1976 | Cooper et al. | 73/194 A |
| 3,974,683 | 8/1976 | Martin | 73/432 PS |

FOREIGN PATENT DOCUMENTS 2,118,150  12/1977  Fed. Rep. of Germany ........ 73/194 A Primary Examiner—Anthony V. Ciarlante
Attorney, Agent, or Firm—Larson, Taylor and Hinds

[57] ABSTRACT

The invention provides a method and apparatus for detecting a bubble in a containing medium such as a liquid, and comprises sending an ultrasonic signal at the bubble at or above the resonant frequency of the bubble, exciting a doppler signal scattered by the bubble in response to the signal, and receiving the doppler signal so as to detect the bubble. The doppler signal may be excited by movement of the bubble, or of that part of the apparatus which receives the doppler signal.

11 Claims, 3 Drawing Figures

DETECTION OF BUBBLES IN A LIQUID

BACKGROUND TO THE INVENTION

This invention relates to methods of and apparatus for, detecting bubbles in a containing medium, and more particularly, but not exclusively bubbles in a liquid such as liquid metal.

SUMMARY OF THE INVENTION

According to one aspect of the present invention, there is provided a method of detecting a bubble in a containing medium, the method comprising arranging for relative movement to occur between the bubble and a receiving means, sending a collimated ultrasonic signal at the bubble from a sending means at a frequency at or above the resonant frequency of the bubble, and detecting a doppler signal scattered by the bubble and received by the receiving means thereby to detect the bubble.

Preferably the doppler scattering is arranged so that a scattered doppler signal received is of pulse form having a peak amplitude proportional to bubble radius and appears as an asymmetric sideband to the ultrasonic signal.

Preferably, the doppler scattering is excited by movement of the bubbles.

According to another aspect of the present invention, there is provided apparatus for detecting a bubble in a containing medium, between which apparatus and bubble relative movement is arranged to occur, the apparatus comprising means for sending an ultrasonic signal at the bubble at a frequency at or above the resonant frequency of the bubble, means for receiving in response to said ultrasonic signal a doppler signal scattered by said bubble, and means for detecting the scattered doppler signal received by the receiving means so as to detect the bubble.

Preferably, the apparatus is adapted for detecting bubbles in a flow of liquid, which liquid may be a liquid metal.

The doppler signal is arranged to appear as an asymmetric sideband to the ultrasonic signal, and the detecting means is arranged to detect asymmetric sidebands, desirably transient asymmetric sidebands.

Preferably, the detecting means is adapted to provide an output pulse having a peak amplitude proportional to bubble radius.

The invention has one application for the detection of bubbles in liquid metal used in the reactor coolant circuit of a nuclear fast reactor.

Gas bubbles in a fluid are resonant features that radiate sound when suitably excited. The influence of a bubble on the propogation of a sound wave is dependent on the resonance properties. If the incident sound has a frequency significantly less than the bubble resonant frequency then little acoustic energy is scattered but the phase velocity of the wave is reduced. On the other hand, if the incident sound has a frequency much higher than resonance, the bubble scatters sound as if it were a solid sphere. Nearer to the resonance frequency, the scattering property is dependent on the damping factor of resonance. It is sufficient to assume that bubbles are ideal spherical scatterers of such incident sounds down to the resonant radius, whilst scattering at the resonance itself in response to such incident sounds is unlikely and can be ignored. The resonant radius is then interpreted as that radius below which the bubble ceases to have a scattering cross-section, and above the resonant radius, the bubble scattering cross-section is its physical cross-sectional area. It may be noted that the resonant sound wavelength can be several orders of magnitude greater than the physical diameter of the bubble.

If a signal is transmitted to a bubble at a frequency above its resonant frequency so that the bubble scatters energy, a doppler effect is produced if there is relative movement between a receiver to receive the scattered signals and the bubble. Such a doppler scattered signal is shifted slightly in frequency and appears as an asymmetric component, or single sideband, to the transmitted signal in the waveband of the signals received by the receiver whereas modulation of the transmitted signal produces symmetrical or double sidebands in the waveband. If all symmetric signals in the waveband are rejected by the receiver, its output is therefore related to the scattered signal of the bubble. By changing the frequencies of the transmitted signals so that a spectrum of scattered signals from bubbles are received, bubble size can be determined when a scattered signal from a particular bubble is no longer received by the receiver, i.e., the frequency of the transmitted signal is below the resonant frequency of the bubble. Since reference tables of resonant frequencies for bubbles of different radii are available, the bubble radius can be read off such a reference table.

The anaylsis equipment may be arranged so that the scattered doppler signal from the bubble is received as a single pulse. The peak amplitude of such a pulse is related in a known manner to bubble radius and may be calibrated fairly accurately when several bubble radii have been determined as aforesaid. Subsequently, the radius of a bubble may be determined simply from a measure of the peak amplitude of the pulse received from a transmitted signal at a single frequency. Since the doppler scattered signal is a transient signal, finer discrimination against interference and noise may be achieved by removing from the signals received by the receiver all non-transient signals.

A count of the pulses received by the receiver from bubbles in the liquid provides a count of those bubbles having a resonant frequency at or below the frequency of the transmitted signal.

BRIEF EXPLANATION OF THE DRAWINGS

The invention will now be particularly described by way of example only with reference to the accompanying drawings in which.

DETAILED DESCRIPTION OF THE INVENTION

Figure 1:
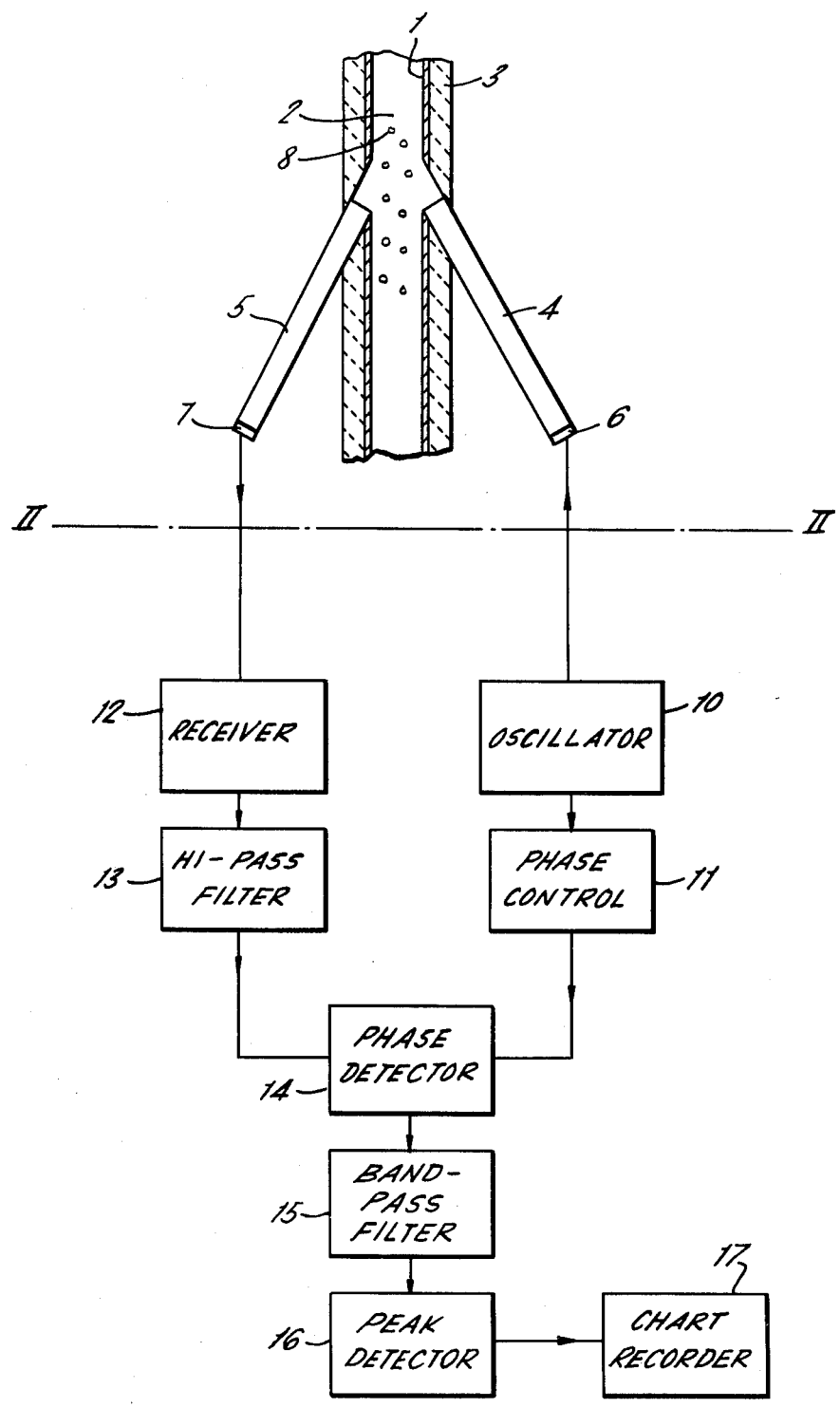
FIG. 1 shows a schematic arrangements of apparatus for detecting bubbles in a liquid sodium stream.

Referring now to FIG. 1, there is shown in median section a stainless steel pipe 1 containing a stream of liquid sodium 2 and having thermal insulation 3 such as rock wool, or MgO, and on one side of the pipe 1 at an oblique angle thereto of about 15°, a steel transmitting waveguide 4, and on the other side of the pipe 1 at a corresponding oblique angle, a steel receiving waveguide 5. A transmitting transducer 6 is disposed at the end of the transmitting waveguide 4 remote from the pipe 1, and a receiving transducer 7 similarly disposed at the end of the receiving waveguide 8. Bubbles 8 flow past the waveguides 4 and 5 in the liquid sodium 2.

An oscillator 10 is connected to provide an output to the transmitting transducer 6 and to a phase control means 11. A receiver 12 is connected to receive an input from the receiving transducer 7 and provide an output to a high-pass filter 13 for removing background noise. Both the filter 13 and the phase control means 11 are connected to a phase detector means 14 for detecting asymmetric sidebands in the waveband of the received signals. The phase detector means 14 provides an output which is fed to a band-pass filter 15 itself connected to a peak detector means 16 which provides a voltage output proportional to pulse height to a chart recorder 17.

In operation, with bubbles 8 flowing past the waveguides 4 and 5 respectively, a collimated signal (e.g., 1 MHz) is transmitted from the transmitting transducer 6 by the transmitting waveguide 4 into the liquid sodium 2. The signal is transmitted by the liquid sodium 2, and a doppler signal is scattered by those bubbles 8 having a resonance frequency below 1MHz as if they were solid spheres. The signal coupled through the pipework and the liquid sodium 2, and the doppler scattered signal, are received by the receiver waveguide 5 and conducted to the receiver transducer 7 to provide an output to the receiver 12. Background noise and other interfering signals are removed by the filter 13 from the output from the receiver 12 and fed to the phase detector means 14. In the phase detector means 14 the phases of the transmitted signal and the output of the filter 13 are adjusted so that they are exactly in phase or antiphase, whereby asymmetric sidebands (i.e., the doppler scattering signal) are passed by the phase detector means 14 but symmetrical sidebands (e.g., signals arising from modulation of the transmitted signal) are rejected. The band-pass filter 15 further limits the frequency range of the asymmetric sidebands to be passed to the peak detector 16 to reduce background noise still further, and the pulses are subsequently displayed on the chart recorder 17. The height of the pulses shown on the chart recorder 17 may be used directly as a measure of the radius of the bubble 8 the pulse represents once the apparatus has been calibrated as aforedescribed by arranging for a scan of transmitted signals to be made over a range of frequencies.

Figure 2:
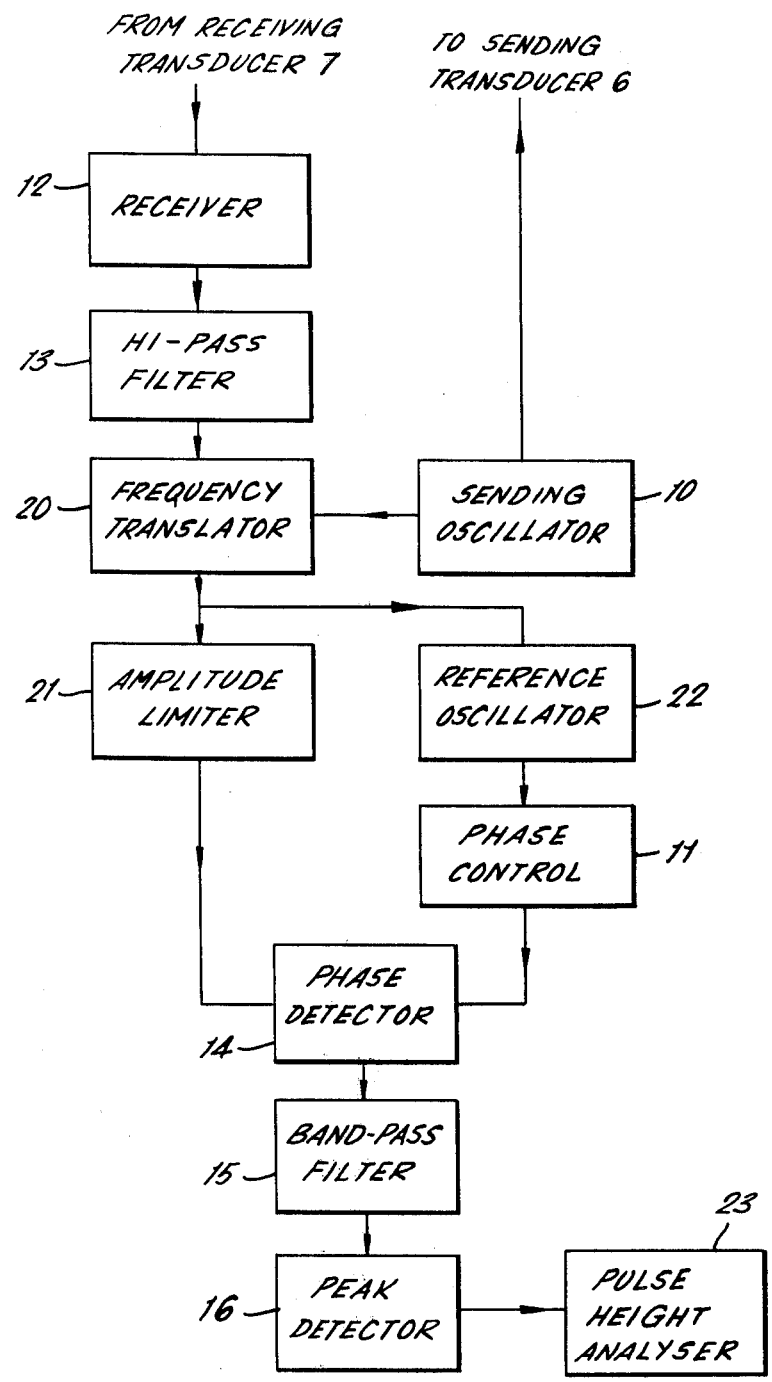
FIG. 2 shows schematically a modification of the arrangement below the line II—II of FIG. 1 to detect transient signals.

In order to improve the stability of the output, the apparatus may be arranged as shown in FIG. 2 to which reference is now made, so that only transient asymmetric sidebands arising from impulsive doppler signals are passed to the peak detector means 16.

In FIG. 2, the oscillator 10 is connected to a frequency translator 20 arranged to receive the output from the high-pass filter 13. The frequency translator 20 reduces the frequency of the signal it receives from the filter 13 (e.g., from 1MHz to 4KHz) to improve stability without changing the symmetry of the sidebands and provides a parallel output to an amplitude limiter 21 and a reference oscillator 22. The amplitude limiter 21 ensures all signals have the same amplitude without changing their phase, the output being fed immediately to one input terminal of a phase detector means 14. The reference oscillator 22 averages the frequency of the output it receives and introduces a delay thereby before providing an output to a phase control means 11 connected to the other input terminal of the phase detector means 14. As the amplitude limiter 21 and the reference oscillator 22 are both operated by an output from the frequency translator 20, only transient signals are detected because of the delay introduced by the reference oscillator 22, matching signals both symmetric and asymmetric being rejected. As in the arrangement of FIG. 1, the output from the phase detector means 14 is passed to a band-pass filter 15 and then to a peak detector means 16, but is finally passed to a pulse height analyzer 23.

It will be appreciated that the sensitivity of the apparatus of FIG. 2 is a function of the relative velocity of the bubbles, the greater the relative velocity the more likely that transient scattered asymmetric signals will be detected, whereas the apparatus of FIG. 1 is substantially independent of the relative velocity of the bubbles.

The waveguides 4 and 5 are desirably machined or welded so as to be integral with the pipe 1 and are arranged to send and receive a collimated signal. The waveguides 4 and 5 may be arranged at alternative angles to the axis of the pipe, for example up to about 30°, and need not be in the same plane provided that their longitudinal axes converge at a point within the pipe 1 at which bubbles are to be detected. By the use of collimated signals, the doppler signal appears as a constant frequency signal because of its brief duration whilst the bubble is at the point of intersection of the axes of the waveguides 4 and 5.

Figure 2A:
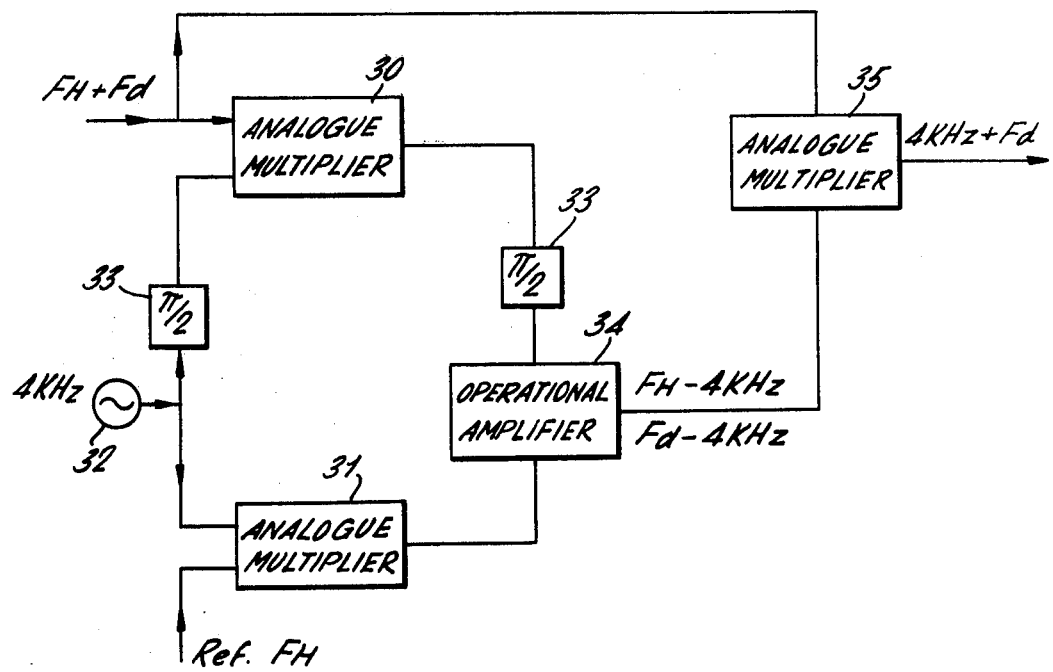
FIG. 2a shows a schematic arrangement of a frequency translator for use in the apparatus of FIG. 2.

The frequency translator 20 of FIG. 2 may be provided by the circuit shown in FIG. 2a to which reference is now made. In FIG. 2a the output from the high-pass filter 13 (not shown) is represented by FH + Fd where:

FH = the coupled signal
Fd = doppler signal and this output is fed to one of two parallel connected analogue multipliers 30 and 31 respectively, the output from the sending oscillator 10 being connected to the other analogue multiplier 31 and represented by FH. A 4KHz reference oscillator 32 has parallel connections to each multiplier 30, 31 but a quadrature unit 33 is connected in series with the connection to multiplier 30 to introduce a quadrature phase change. The outputs from the multipliers 30 and 31 are connected to an operational amplifier 34, another quadrature unit 33 being inserted between multiplier 30 and the operational amplifier 34 to introduce another quadrative phase change. The output from the operational amplifier 34 contains the mixed signals FH — 4KHz and Fd — 4KHz and is connected to a multiplier 35 which also receives as an input the output from the filter 13, the output from the multiplier 35 then representing the reference oscillator 32 signal and the doppler signal, i.e., 4KHz + Fd.

It is necessary that the reference signal used is not of square wave form and this will determine the selection of the phase control means 11.

EXAMPLE I

The apparatus of FIG. 1 was constructed using the following proprietory equipment, or designs:

| Items | |
|---|---|
| Transducers (6) and (7) | Lead Zirconium Titanate Piezo - electric Transducers |
| Receiver (12) ) | Ortec-Brookdeal |
| Hi-Pass Filter (13) ) | Low noise Amplifier |

-continued

| Items | |
|---|---|
| Oscillator (10) | Type 9452 Wavetek Waveform Generator - Type 134 |
| Phase control (11) | Ortec - Brookdeal Phase Shifter - Type 9421 |
| Phase detector (14) | Ortec - Brookdeal Phase Detector - Type 9412A but connected so that the role of reference and signal are reversed in use. |
| Band pass filter (15) | Barr & Stroud Active Filter Type EF2 |
| Peak Detector (16) | Constructed in accordance with pages 132 et seq of: "Applicatons of Operational Amplifiers - Third Generation Techniques" by Burr-Brown Inc which is incorporated by reference herein. |
| Chart Recorder (17) | Devices Recorder Type MR2 |

EXAMPLE II

The apparatus of FIG. 2 was constructed using the following equipment:

| | |
|---|---|
| Amplitude Limiter (21) | Provided by the Ortec - Brookdeal Phase Detector Type 9412A used for Phase Detector (14) |
| Reference Oscillator (22) | Signetics Phase Locked Loop Type 561B |
| Pulse Height Analyser (23) | Datalab Micro 4 |

The equipment used for items (10-16) was the same as that used for the apparatus of FIG. 1.

The frequency translator 20 of FIG. 2 as shown in FIG. 2a was provided by the following equipment:

| | |
|---|---|
| Analogue Multiplier (30) (31) & (35) | Motorola Multipliers Type MC 1495L |
| Operational Amplifier (34) | Signetics Differential Video Amplifier Type 5733 |
| Reference Oscillator (32) | Conventional Wien-bridge Oscillator using Signetics Operational Amplifier Type 5558 |
| Quadrature Units (33) | Conventional Phase-Shifter using Signetics Differential Video Amplifier Type 5733 Alternatively, the Quadrature Unit (33) connected between the Reference Oscillator (32) and the Analogue Multiplier (30) may be provided by a Signetics Operational Amplifier Type 5558. |

Examples of phase-shift circuits and Wien-bridge oscillator circuits are also given in the aforementioned publication incorporated herein: "Applications of Operational Amplifiers — Third Generation Techniques" by Burr-Brown Inc.

It will be appreciated that the invention has advantages in applications where bubbles are to be detected in a hostile environment, such as a liquid metal, and enables the waveguide to be in direct contact with the liquid.

The invention may also be applied to applications where relative motion is introduced between the receiver and the bubble by moving the receiver.

Although the invention has been described in relation to the detection of bubbles in liquid metal, the invention may also be used to detect bubbles in liquids in other hostile environments, for example of temperature and/or corrosion.

I claim:
1. Apparatus for detecting a bubble in a liquid stream contained in a metal duct and comprising,
   (a) a transmitter waveguide;
   (b) an ultrasonic sending transducer disposed at one end of the transmitter waveguide for sending an ultrasonic signal of 1MHz through the waveguide;
   (c) a receiver waveguide;
   (d) a receiving transducer at one end of the receiver waveguide, the waveguides being disposed one on one side and one on the other side of the duct and of the same material and integral with the duct as the other end of the waveguides, each waveguide being at the same angle of between 15° to 30° to the longitudinal axis of the duct;
   (e) a sending oscillator connected to the sending transducer;
   (f) a receiving means for receiving a signal from the receiving transducer;
   (g) a first high-pass filter for removing background noise to which the receiving means provides an output in response to the signal from the receiving transducer;
   (h) a frequency translator which is arranged to receive an output signal from the first high-pass filter, and from the sending oscillator, and is arranged to reduce the frequency of the signal it receives from the high-pass filter to 4 KHz;
   (i) an amplitude limiter to which the frequency translator provides an output and which ensures that all signals therefrom have the same amplitude without changing the phase thereof;
   (j) a reference oscillator to which the frequency translator also provides an output and which averages the frequency of the output it receives and introduces a delay thereby;
   (k) a phase control means to which the reference oscillator provides an output;
   (l) a phase detector means for detecting and accepting transient asymmetric sidebands in the waveband of signals it receives from the amplitude limiter and the phase control means and rejecting both symmetric and non-transient asymmetric signals thereof;
   (m) a second high-pass filter for receiving an output from the phase detector means to limit the frequency range of the output signal from the second high-pass filter;
   (n) a peak detector means for receiving an output signal from the second high-pass filter, and
   (o) a pulse height analyser for receiving an output from the peak detector means.
2. Apparatus for detecting a bubble in a containing medium wherein relative movement between said apparatus and said bubble is arranged to occur, said apparatus comprising:
   (a) means for sending a collimated ultrasonic signal at the bubble at a frequency at or above the resonant frequency of the bubble;
   (b) means for receiving in response to said ultrasonic signal a doppler signal scattered by said bubble, and
   (c) means for rejecting symmetric sidebands and accepting asymmetric sidebands in the signal received by the receiving means so as to detect said bubble.

3. Apparatus as claimed in claim 2, wherein the sending means and the receiving means both comprise waveguide means disposed at the same oblique angle about the relative path of the bubble and such that the longitudinal axes of both said waveguide means converge on and meet substantially on said path.

4. Apparatus as claimed in claim 2, further comprising, means for reducing the frequency of the signal received by the receiving means without changing the symmetry of the sidebands in said signal.

5. Apparatus as claimed in claim 2, further comprising a metal duct for containing a liquid which provides the containing medium, the sending means and receiving means both comprising waveguide means and being integral with the duct and of substantially the same material as the duct.

6. Apparatus as claimed in claim 2, including means for rejecting non-transient asymmetric sidebands in the signal received by the receiving means.

7. Apparatus as claimed in claim 2, including means for counting the asymmetric sidebands accepted by the receiving means with respect to time so as to provide a count of the bubbles detected by the apparatus in said time.

8. A method of detecting a bubble in a containing medium, the method comprising:
 (a) arranging for relative movement to occur between the bubble and a receiving means;
 (b) sending a collimated ultrasonic signal at the bubble at or above the resonant frequency of the bubble;
 (c) rejecting symmetric sidebands and accepting asymmetric sidebands in the signal received by the receiving means so as to detect the bubble.

9. A method as claimed in claim 8, including rejecting non-transient asymmetric sidebands and accepting transient asymmetric sidebands in the signal received by the receiving means.

10. A method as claimed in claim 8, including relating the received signal to bubble size by reducing the frequency of the ultrasonic signal, and relating the amplitude of the asymmetric sideband in the received signal to the radius of a bubble having a resonant frequency the same as the lowest frequency of the ultrasonic signal at which an asymmetric sideband is received by the receiving means.

11. A method as claimed in claim 8, including counting the asymmetric sidebands in the signals accepted by the receiving means with respect to time so as to provide a count of the bubbles detected during said time.

* * * * *